United States Patent
Aloise et al.

(10) Patent No.: US 6,783,438 B2
(45) Date of Patent: Aug. 31, 2004

(54) METHOD OF MANUFACTURING AN ENDODONTIC INSTRUMENT

(75) Inventors: Carlos A. Aloise, Chino, CA (US); Gary T. Garman, La Verne, CA (US)

(73) Assignee: Ormco Corporation, Orange, CA (US)

( * ) Notice: Subject to any disclaimer, the term of this patent is extended or adjusted under 35 U.S.C. 154(b) by 153 days.

(21) Appl. No.: 10/125,673

(22) Filed: Apr. 18, 2002

(65) Prior Publication Data

US 2003/0199236 A1 Oct. 23, 2003

(51) Int. Cl.$^7$ ................................................ B24B 1/00
(52) U.S. Cl. ....................................................... 451/48
(58) Field of Search ........................... 451/48, 28, 540; 433/81, 102, 224

(56) References Cited

U.S. PATENT DOCUMENTS

| | | |
|---|---|---|
| 3,174,851 A | 3/1965 | Buehler et al. |
| 3,351,463 A | 11/1967 | Rozner et al. |
| 4,888,863 A | 12/1989 | Cox et al. |
| 5,044,947 A | 9/1991 | Sachdeva et al. |
| 5,429,501 A | 7/1995 | Farzin-Nia et al. |
| 5,655,950 A | 8/1997 | Heath et al. |
| 5,762,541 A | 6/1998 | Heath et al. |
| 5,857,852 A | 1/1999 | Garman |
| 5,882,198 A * | 3/1999 | Taylor et al. ............... 433/102 |
| 5,941,760 A * | 8/1999 | Heath et al. ............... 451/48 |
| 5,964,770 A | 10/1999 | Flomenblit et al. |

(List continued on next page.)

FOREIGN PATENT DOCUMENTS

| | | |
|---|---|---|
| EP | 0 287 267 | 10/1988 |
| WO | WO 99 37235 | 7/1999 |

OTHER PUBLICATIONS

Shape Memory Alloys, *ASM Handbook, vol. 2, Properties and Selection: Nonferrous Alloys and Special–Purpose Materials*, pp. 897–902, 1992.

Tobushi et al., *Recovery Stress Due to R–Phase Transformation in Ni–Ti Shape Memory Alloy*, Proceedings of First Int'l Conf. on Shape Memory and Superelastic Technologies, Asilomar Conference Ctrl, Pacific Grove, CA, USA, pp. 163–168, 1994.

*Primary Examiner*—Dung Van Nguyen
(74) *Attorney, Agent, or Firm*—Wood, Herron & Evans, LLP

(57) ABSTRACT

Method for manufacturing endodontic instruments having either helical or non-helical flutes. A method is provided for forming superelastic endodontic instruments having helical flutes, wherein a wire of superelastic material is formed into an instrument blank, and before twisting, the superelastic alloy is brought to an annealed state comprising a phase structure including a rhombohedral phase alone or in combination with austenite and/or martensite, or a combination of martensite and austenite. In this annealed state, the instrument blank is twisted at low temperature, for example less than about 100° C., and advantageously at ambient temperature to the final desired twisted configuration. The twisted instrument is then heat treated and rapidly quenched to a superelastic condition. A method is further provided for manufacturing endodontic instruments having either helical or non-helical flutes with hard surfaces and resilient cutting edges by either an EDM or ECM process, wherein material is removed from the instrument blank in the desired flute pattern. The EDM or ECM process disintegrates the surface material, and as it cools, at least a portion of the removed material re-deposits onto the surface being machined to form a recast layer having a surface hardness that is at least about 15% greater than the hardness of the material forming the instrument blank. A method is further provided in which an EDM or ECM process is used to form an instrument blank, followed by twisting at low temperature.

47 Claims, 4 Drawing Sheets

U.S. PATENT DOCUMENTS

| | | |
|---|---|---|
| 5,984,679 A | 11/1999 | Farzin-Nia et al. |
| 6,036,708 A | 3/2000 | Sciver |
| 6,131,579 A | 10/2000 | Thorson et al. |
| 6,149,501 A | 11/2000 | Farzin-Nia et al. |
| 6,158,304 A | 12/2000 | Packer et al. |
| 6,165,210 A | 12/2000 | Lau et al. |
| 6,293,020 B1 | 9/2001 | Julien |
| 6,299,445 B1 | 10/2001 | Garman |
| 6,315,558 B1 | 11/2001 | Farzin-Nia et al. |
| 2002/0137008 A1 * | 9/2002 | McSpadden et al. ........ 433/102 |

* cited by examiner

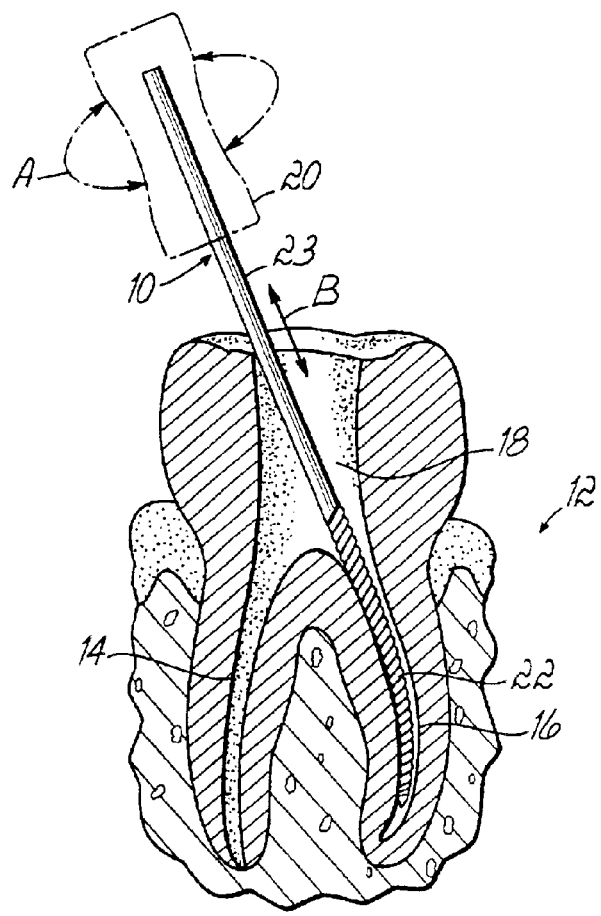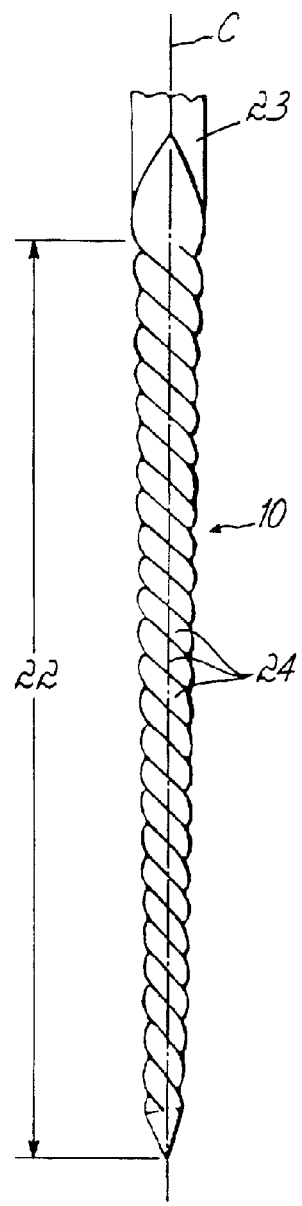
FIG. 1
FIG. 1A

METHOD OF MANUFACTURING AN ENDODONTIC INSTRUMENT

FIELD OF THE INVENTION

The present invention generally relates to endodontic instruments, such as files and reamers, and more specifically, to those instruments especially useful in root canal procedures.

BACKGROUND OF THE INVENTION

Endodontists use various types of instruments for cleaning and enlarging the root canals of the teeth. In a typical root canal procedure, an endodontist first makes an opening in the surface of the tooth to provide access to the interior. The endodontist then utilizes small instruments, such as hand-held files and reamers, to clean and enlarge the narrow, tapered root canals. In a conventional procedure, the endodontist fills the prepared root canals with gutta percha, which is a rubber-like substance, and then seals the tooth with protective cement. The endodontists may sometimes apply a crown to the tooth as a final step.

Typically, the endodontist uses a series of delicate, flexible files to clean out and shape the root canals. Each file includes a proximal end, typically including a handle to be gripped between the fingers of the endodontist, and a distal end or tip. A working length with helical or non-helical flutes and cutting edges is located between the proximal and distal ends. The endodontist uses files of increasingly larger diameter to sequentially increase the diameter of the root canal and achieve the desired diameter and shape.

Endodontic instruments of the desired type having helical flutes are conventionally fabricated by permanently twisting a rod of triangular, square, or rhomboid-shaped cross section. The angles formed between the surfaces form the cutting edges which spiral along the working length of the instrument. Another method for manufacturing instruments of the described type having either helical or non-helical flutes is by a machining process wherein an instrument blank is moved past a rotating grinding wheel. The instrument blank is thereafter indexed and again moved past the grinding wheel, and these steps are repeated as many times as are necessary to form the instrument blank into the desired cross section. The flute grinding process, however, produces a directional surface finish along the cutting axis which propagates early material failure, introduces machining stresses into the material, and cuts across the grain structure of the instrument blank. In addition, these direct grinding methods are time consuming and expensive. They also limit the variety of cross-sectional shapes that may be formed in the final product.

Over the past several years, endodontic instruments having helical flutes have been manufactured by simultaneously grinding and twisting thin carbon steel or stainless steel rods or wires. Specifically, steel wire blanks are first ground to the desired cross sectional shape, such as square, triangular or rhomboid, and to the appropriate size and taper. The ground blank is then gripped at one end and spring loaded jaws are brought into contact with the ground portion of the blank. As the blank is rotated from the gripped end, the jaws are moved axially away from that end. The jaws therefore twist the rotating blank and form helical flutes into the blank. The longitudinal, ground edges of the blank form helical cutting edges on the file. The axial jaw speed, twisting speed and spring force are controlled to obtain the desired helical configuration.

Carbon and stainless steel instruments are generally stiff, which may lead to errors during root canal therapy. With the emergence of superelastic materials, such as nickel-titanium alloys, endodontic instrument manufacturers are now able to form endodontic root canal files and reamers with much more flexibility. This greatly assists the endodontist during use of the file or reamer in a root canal procedure. The use of superelastic material, however, causes some significant manufacturing concerns due to the tendency of the material to return to its original shape after the release of an applied force. File or reamer blanks manufactured of superelastic materials generally react in this manner to the conventional twisting methods employed for manufacturing carbon and stainless steel files and reamers. Moreover, if superelastic blanks are over-stressed, such as by being twisted too much during the fluting procedure, the material is subject to failure. For reasons such as these, current manufacturers of endodontic instruments may resort to grinding the helical profile directly into the superelastic blanks while applying no twisting forces to the blanks. These direct grinding methods are time consuming and expensive. They also limit the variety of cross sectional shapes that may be formed in the final product.

In U.S. Pat. No. 6,149,501, a method is provided for manufacturing superelastic endodontic instruments in which a blank is provided and maintained in the austenite phase, preferably above the austenite finish temperature (Af), at least prior to a twisting operation and, preferably, prior to and during the twisting operation. During the twisting operation, the material is converted from the austenite phase to the martensite phase by the stress applied during the twisting operation. Thus, the superelastic material undergoes stress-induced martensite transformation from a 100% austenite phase. For this method, high temperature tooling is required because the twisting operation is performed at a temperature above the Af temperature. The tooling and file blank are preferably submerged in a heated liquid, such as an oil or salt solution at a temperature of 500° C. or above, to bring the material to a 100% austenite phase. The heated liquids, however, are generally corrosive to the tooling.

With the above background in mind, there is a need for endodontic instruments, such as files and reamers, and to methods of fabricating such endodontic instruments that avoids the disadvantages described above for grinding and/or twisting techniques, that provides an instrument having either helical or non-helical flutes, and that is flexible and highly resistant to torsional breakage. It would further be desirable to provide a method of manufacturing a wide variety of superelastic endodontic instruments using a twisting technique that does not require high temperature tooling.

SUMMARY OF THE INVENTION

The present invention provides a method for forming superelastic endodontic instruments in which helical flutes may be formed in a blank by twisting the instrument blank at low temperature, for example a temperature less than about 100° C., and advantageously at ambient temperature. To this end, wire of superelastic material, such as a nickel-titanium alloy wire, is formed into an instrument blank, wherein before twisting, the superelastic material is brought to an annealed state comprising a phase structure that is a rhombohedral phase, a combination of an austenite phase and a martensite phase, a combination of a rhombohedral phase and an austenite phase, a combination of a rhombohedral phase and a martensite phase, or a combination of a rhombohedral phase, an austenite phase and a martensite phase. In this annealed state, the instrument blank is twisted at low temperature to the final twisted configuration desired for the instrument. The twisted instrument is then heat treated, for example at a temperature of at least about 300° C., followed immediately by rapid quenching to a superelastic condition. To provide the superelastic material in the annealed state, the material may be annealed at a temperature in the range of about 250–700° C., and advantageously at about 350–550° C., then cooled to ambient temperature. This annealing may be performed before forming the alloy wire into an instrument blank, or after the instrument blank has been formed. After rapidly quenching the twisted instrument, the method may further comprise a stress relieving heat treatment, for example at a temperature in the range of about 150–300° C. for a period of about 2–6 hours.

The present invention further provides a method for manufacturing endodontic instruments having either helical or non-helical flutes, having hard surfaces with a non-directional surface finish and resilient cutting edges, and having both flexibility and resistance to torsional breakage. To this end, flutes are formed in an instrument blank by either EDM or ECM. EDM refers to machining methods including electrical discharge machining, wire electrical discharge machining and electrical discharge grinding. ECM refers to electrochemical machining. Using either an EDM or ECM process, material is removed from the instrument blank in the desired flute pattern with at least about 25% of the diameter of the instrument blank being removed at a point of maximum metal removal. The EDM or ECM process disintegrates the surface material, and as it cools, at least a portion of the removed material re-deposits onto the surface being machined, i.e. onto the flutes being formed, to form a recast layer. The recast layer on the instrument has a surface hardness that is at least about 15% greater, such as about 15–25% greater, than the hardness of the material forming the instrument blank. Thus, surface hardness is increased along the flutes, which provides a significantly harder and more resilient cutting edge for the endodontic instrument. Additionally, the EDM or ECM process produces a non-directional surface finish, thereby avoiding inducement of early material failure propagated by the directional surface finish that results from conventional grinding techniques.

In one exemplary method of the present invention, by rotating the instrument blank about its center longitudinal axis, while advancing the instrument blank past an electrode, helical flutes may be formed. In an alternative exemplary method of the present invention, by holding the instrument blank stationary while advancing an electrode past the instrument blank, non-helical flutes in axial alignment may be formed. There is thus provided a method for efficiently producing precision endodontic instruments with minimal distortion, non-directional surface finish, and with hardened cutting edges along the working length of the instrument in both helical and non-helical flute designs.

The present invention further provides a method in which the instrument blank is formed by EDM or ECM, followed by twisting the blank at low temperature to form helical flutes, thereby providing a low temperature twisting method with the benefits of surface finish and hardness achieved by EDM and ECM.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

FIG. 1 is a cross-sectional view of a tooth and an endodontic instrument in accordance with the invention shown in use within a root canal.

FIG. 1A is a side view of an endodontic instrument in accordance with the invention having helical flutes.

DETAILED DESCRIPTION

Figure 1B:
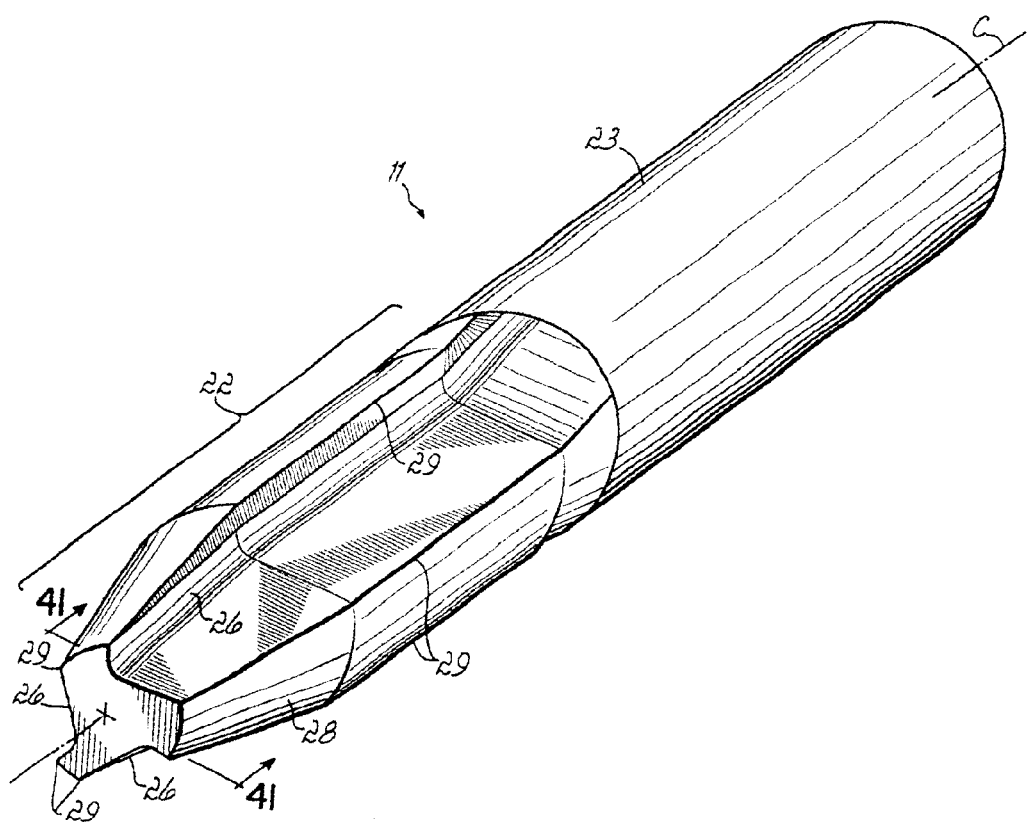
FIG. 1B is a perspective view of an endodontic instrument in accordance with the invention having non-helical flutes.

Throughout the figures, like reference numerals are used to refer to like parts. Referring first to FIG. 1, an endodontic instrument 10 constructed in accordance with an embodiment of the present invention is shown being used during a root canal procedure on a tooth 12. Tooth 12 includes root canals 14, 16 and an upper interior portion 18 which has been initially opened using another instrument, such as a drill (not shown). Instrument 10 includes a handle 20 for manual gripping by, for example, an endodontist and a working length 22 having flutes, as will be discussed in more detail below. Although these instruments are typically manipulated manually, the invention may be adapted to power-operated instruments as well. In a conventional manner, instrument 10 may be rotated in the direction of arrows "A" and reciprocated in the direction of arrow "B" by the endodontist to clean out and enlarge root canal 16. The working length 22 of the instrument 10 may include helical flutes 24, as depicted in FIGS. 1 and 1A. Alternatively, an instrument 11 may be used in which the working length 22 comprises non-helical flutes 26, as depicted in FIG. 1B. Helical flutes 24 spiral around the center longitudinal axis C of the instrument 10, whereas non-helical flutes 26 extend along the center longitudinal axis C of the instrument 11 in axial alignment.

Instruments of the present invention advantageously comprise a superelastic material. Superelastic materials are typically metal alloys which return to their original shape after substantial deformation. Superelastic alloys, such as nickel-titanium (NiTi) alloys, can withstand several times more strain than conventional materials, such as stainless steel, without becoming plastically deformed. Further, a superelastic material will generally recover approximately 6% after twisting at ambient temperature while a stainless steel will recover only 1–2% after twisting. Typically, superelastic alloys undergo a stress-induced martensitic transformation which allows for shape memory properties. It may be appreciated by one skilled in the art that superelasticity is a function of composition and materials processing, and so a material is superelastic if its composition and processing history are such that it is capable of exhibiting superelastic properties. Shape memory and superelasticity may be found in stoichiometric NiTi, near-equiatomic Ni—Ti, for example 50.8 at. % Ti and 49.2 at. % Ni, Ni—Ti—Cu, Ni—Ti—Nb and Ni—Ti—Fe alloys as well as beta-phase titanium or other Ti based alloys. Superelastic material for use in the present invention advantageously comprise at least about 40 at. % titanium. By way of further example, the superelastic material may be nickel-titanium or a nickel-titanium alloy further comprising niobium, copper, iron, chromium, cobalt, vanadium, hafnium or palladium. While not intending to be bound, NiTi alloys used in the present invention advantageously comprise about 52–57 at. % Ni for providing optimal shape memory and superelastic properties. For example, an exemplary alloy comprises 54–55 at. % Ni, balance Ti or balance Ti and one or more other alloy elements. Further exemplary alloys include 54Ni-46Ti and 41Ni-50Ti-9Nb.

The specific alloy composition used for the endodontic instrument of this invention is not critical, as the invention may utilize many materials which exhibit superelastic characteristics. For example, U.S. Pat. Nos. 5,044,947 and 5,429,501, which are incorporated by reference herein in their entirety, disclose nickel-titanium-copper alloys and beta-phase titanium alloys, respectively, and U.S. patent application Ser. No. 08/839,965 entitled Ni—Ti—Nb ALLOY PROCESSING METHOD AND ARTICLES FORMED FROM THE ALLOY, incorporated by reference herein in its entirety, discloses NiTiNb alloys.

The present invention provides a method for forming superelastic endodontic instruments, such as files and reamers, wherein a twisting operation is performed at low or ambient temperature, thereby eliminating the need for high temperature resistant tooling and corrosive high temperature salt baths. By eliminating the high temperature twisting operation, the twisting equipment traditionally used for stainless steel materials may be used in the method for forming superelastic endodontic instruments, such as those made from nickel-titanium alloys. In addition, by eliminating the high temperatures and corrosive liquid baths, a safer process is provided.

The first part of the method of the present invention involves providing an instrument blank in which the superelastic material, such as a nickel-titanium alloy, is in an annealed state comprising a phase structure including a rhombohedral phase, a combination of the rhombohedral phase with either or both of martensite and austenite, or a combination of the austenite phase and martensite phase. To obtain the blank in the annealed state, a two-step process is performed in which either step may be carried out first. One of the two steps involves forming the blank from a wire of superelastic material. The blank may be formed by EDM, including electrical discharge machining, wire electrical discharge machining, and electrical discharge grinding, or by ECM, as will be discussed further below. Alternatively, the instrument blank may be formed by grinding. However, EDM/ECM processes offer certain advantages in the formation of endodontic instruments, as will be described in further detail below. For example, the EDM/ECM processes reduce or eliminate machining stresses induced by grinding methods and produce non-directional surface finishes thereby avoiding inducing early material failure propagated by directional surface finishes that result from grinding methods.

The other step in the two-step process for providing the instrument blank in the annealed state is an annealing step, which may be performed on the wire prior to forming the instrument blank, or may be performed on the instrument blank after its formation. The annealing step involves annealing the alloy at a temperature and for a time sufficient to bring the alloy to a state having a desired phase structure between 100% austenite and 100% martensite. The phase structure advantageously includes a rhombohedral phase. The rhombohedral phase may be the only phase, or the phase structure may further include austenite and/or martensite. Alternatively, the phase structure may be a combination of austenite and martensite. As may be understood by one skilled in the art, annealing refers to the heating of an alloy to a temperature and maintaining that temperature for a time sufficient to bring about a desired change in the alloy. The temperature sufficient for inducing the desired phase structure is dependent upon the particular alloy, but is generally in the range of about 250–700° C. for currently known superelastic materials, and is advantageously in the range of about 350–550° C. The time sufficient for inducing the desired phase structure is also dependent upon the particular alloy and the size of the wire or blank, as may be appreciated by one skilled in the art. Generally, the annealing time ranges from about 15 seconds to about 20 minutes, for example about 30 seconds to about 2 minutes. By way of further example only, and not limitation, a 1 mm diameter wire may be annealed at a temperature about 495° C. for a period of 15 seconds to induce a phase comprising 90%≦austenite<100%, the remainder rhombohedral phase. Following the anneal, the material is cooled to room or ambient temperature, upon which it remains in the annealed state comprising the desired phase structure. By this two-step forming and annealing method, there is provided an instrument blank in an annealed state comprising a superelastic material in a rhombohedral phase alone or in combination with austenite and/or martensite, or in a phase structure that is a combination of austenite and martensite.

By this two-step method, it may be understood that the manufacturer of endodontic instruments may obtain nickel-titanium alloy wires, for example, in the annealed state, whereby the wire manufacturer performs the annealing treatment, and the endodontic instrument manufacturer forms the instrument blank and subsequently twists the blank to form the fluted instrument. Alternatively, the endodontic instrument manufacturer may obtain the wire in a non-annealed state, and perform the annealing treatment as part of the instrument manufacturing process.

The method of the present invention further comprises twisting the instrument blank in its annealed state at low temperature, for example a temperature less than about 100° C. to a final twisted configuration for the endodontic instrument. Advantageously, the twisting step is performed at ambient temperature, thereby eliminating the need for immersion of the blank and tooling equipment into high temperature salt baths or exposing them to other high temperature methods. The low temperatures, for example up to about 100° C., also eliminate the excessively high temperatures used in the prior art. Thus, a conventional heat-treat oven may be used for the low temperature heating, rather than salt baths or other high temperature heating methods.

Figure 2:
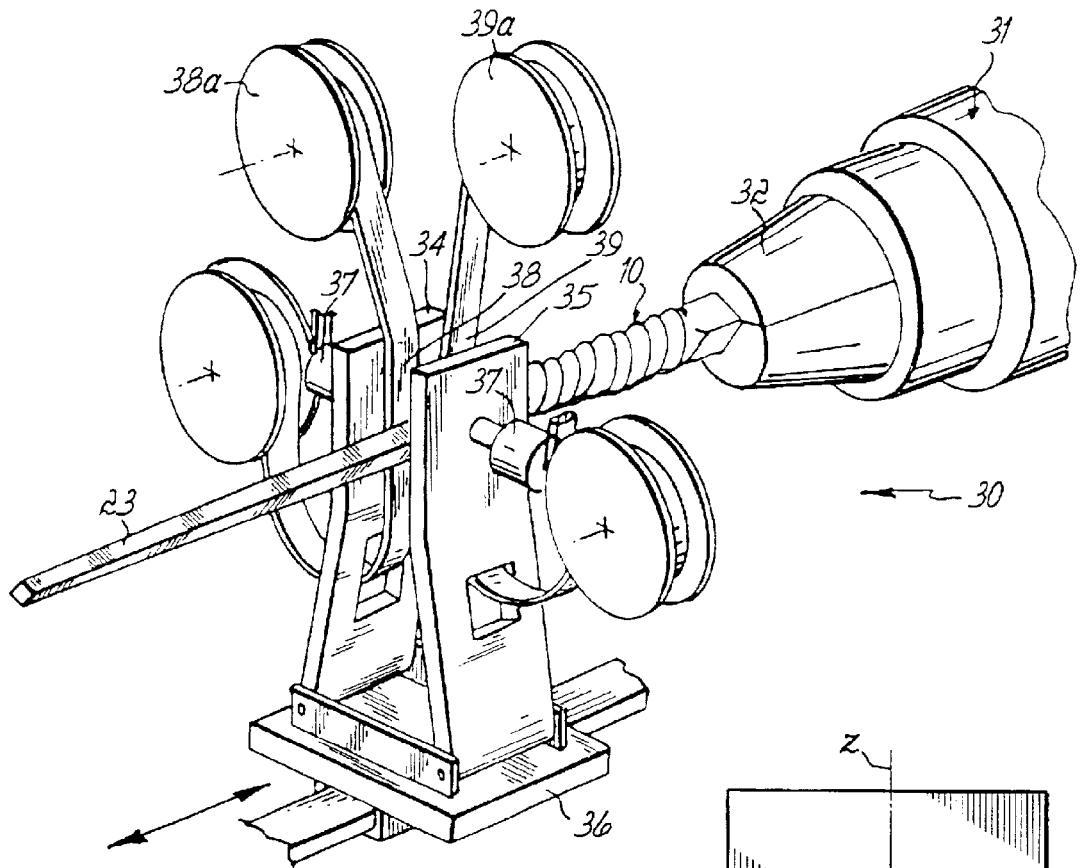
FIG. 2 is a schematic perspective view of one type of apparatus used in fabricating a superelastic file in accordance with the present invention.

The twisting operation of the method of this invention may be implemented, for example, with an apparatus such as apparatus 30 depicted in FIG. 2. The twisting apparatus 30 includes a drive head 31 which rotates about a horizontal axis. Extending from the drive head 31 is a collet 32 which circumferentially grips and secures the proximal or inner end of a preformed instrument blank 23 for rotation about the longitudinal axis thereof. The distal or outer end portion of the instrument blank 23 is secured by opposing jaws 34, 35, which are mounted on a stage 36 that moves parallel to the longitudinal axis of the instrument blank (horizontally as shown in FIG. 2), away from collet 32 at a predetermined rate as the collet rotates to twist the instrument blank 23 to form a twisted instrument, such as the helically fluted file 10 depicted in FIG. 1A. At least one of the jaws includes a spring or air cylinder 37 so that it may be compressed against the opposing jaw with a constant force. Each jaw 34, 35 includes a protectant layer 38, 39 which is malleable and able to withstand the working temperature of the file blank 23, which may be up to about 100° C., for example. Brass is one material known to be suitable. With subsequent files formed, the jaws 34, 35 may be provided, if necessary, with a new protectant layer 38, 39 from a source 38a, 39a such as take-off reels. It may be appreciated by one skilled in the art that apparatus 30 is merely exemplary of twisting apparatuses that may be used in the method of the present invention, and that other apparatuses, now known or hereafter developed, may be used for the twisting operation with departing from the scope or spirit of the invention.

After the instrument blank is twisted to its final configuration, the twisted instrument is heat treated, followed by rapidly quenching the twisted instrument to a superelastic condition. The heat treatment may be at a temperature in the range of about 300–800° C., for example in the range of about 400–600° C. The heat treatment may be by a conventional heat-treat oven, electrical heating, inductance heating or by submerging the twisted instrument in a heated liquid. The rapid quenching immediately follows the heat treatment whereby the instrument is cooled within a fraction of a second to a few seconds to a superelastic condition.

The twisted instrument may be further subjected to a stress relieving heat treatment after quenching. To relieve stress within the material, the instrument may be heated, for example, to a temperature of about 150–300° C., such as by a conventional heat-treat oven, electrical heating, inductance heating or by submerging in a heated liquid. The stress relieving heat treatment may be performed, for example, for about 2–6 hours.

By the method of the present invention, there is thus provided a superelastic endodontic instrument, such as a file or reamer, having higher torsional and bending flexibility compared to conventional steel instruments, and manufactured by improved processes relative to prior superelastic instrument production techniques. Generally, the invention provides a process in which a superelastic endodontic instrument blank may be formed by EDM, ECM or ground and then twisted at ambient or low temperature to produce a fluted instrument having superelastic properties. By this invention, high temperature tooling requirements are eliminated for the twisting operation.

Figure 3:
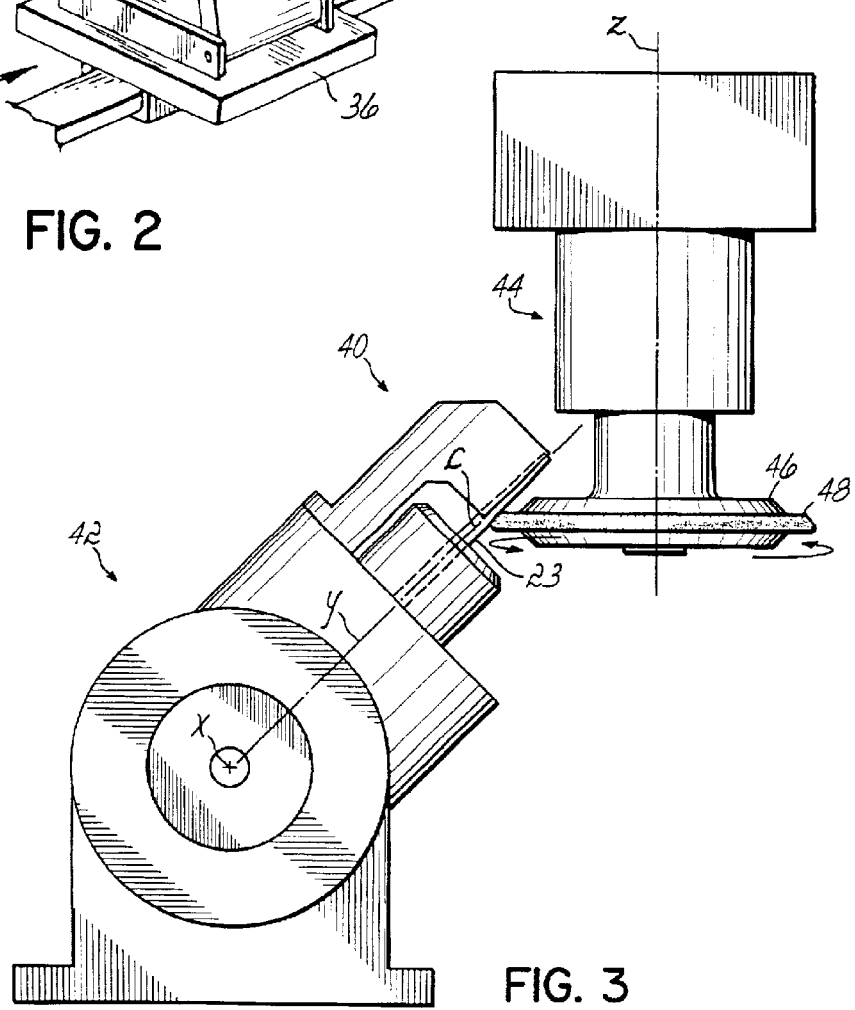
FIG. 3 is a schematic side view of an exemplary apparatus for forming endodontic instruments in accordance with the present invention.

The EDM/ECM method of the present invention may be implemented with an apparatus such as apparatus 40 depicted in FIG. 3. Prior to forming the flutes, cylindrical rods or wires may be formed into instrument blanks 23, if desired. In one embodiment of the method of the present invention, the instrument blank 23 may be formed by an EDM or ECM method. In another embodiment of the present invention, the instrument blank may be formed by traditional techniques, such as grinding. Apparatus 40 is one example of an EDM/ECM apparatus for carrying out the method of the present invention. Apparatus 40 includes a "V" block support 42 with a simultaneous titling axis X at 30–46° movement and a rotating axis Y at 360° movement. The "V" block support 42 is shown rotated 90° for clarity. Apparatus 40 further includes a machine spindle 44 rotatable about the center axis Z and having an electrode holder 46 for supporting a circular electrode 48. It may be appreciated by one skilled in the art that the electrode is a cathode in ECM methods. The instrument blank 23 is held in the "V" block support 42 and adapted to be rotated about the central longitudinal axis C by rotating the "V" block support 42 about rotating axis Y. The movement of the instrument blank 23 and the electrode 48 may be in accordance with a pre-programmed path, digitally controlled by a CNC controller (not shown), to generate a flute pattern in accordance with a pattern programmed into the controller.

To form an endodontic instrument 10 having helical flutes 24, such as instrument 10 in FIG. 1A, the instrument blank 23 is held in the "V" block support 42 which is an indexing fixture, and the blank 23 is rotated about its center longitudinal axis C. While rotating, the instrument blank 23 is advanced past electrode 48 while the electrode is either held stationary or rotated about center axis Z. The instrument blank 23 is advanced past the electrode 48 at a relatively slow feed rate, for example about 0.25 to about 4 inches/minute so that the electrode 48 removes at least about 25% of the diameter of the instrument blank 23 at the point of maximum metal removal and forms a helical surface or flute 24 on the instrument blank 23. The instrument blank 23 is then rotatably indexed about its center longitudinal axis C not more than 180° by rotating "V" block support 42, and the instrument blank 23 is again advanced past the electrode 48 to form a second helical surface or flute 24 on the instrument blank 23. The indexing and flute forming steps may be repeated as many times as are necessary to form the desired number of flutes 24 on the endodontic instrument 10.

To form an endodontic instrument 11 having non-helical flutes 26, such as instrument 11 in FIG. 1B, the instrument blank 23 is held stationary by "V" block support 42 and the electrode 48 is advanced at a relatively slow feed rate past the stationary instrument blank 23 so that the electrode removes at least about 25% of the diameter of the instrument blank 23 at the point of maximum metal removal and forms a non-helical surface or flute 26 on the instrument blank 23. By non-helical, it is meant that the flutes are aligned axially. The instrument blank 23 is then rotatably indexed about its center longitudinal axis C not more than 180° by rotating "V" block support 42, and the electrode 48 is again advanced past the instrument blank 23 to form a second non-helical flute 26. The indexing and flute forming steps are repeated as many times as are necessary to form the desired number of non-helical flutes 26 on the endodontic instrument 11.

EDM and ECM processes offer a distinct advantage over traditional grinding techniques in manufacturing endodontic instruments. The EDM and ECM processes disintegrate material without direct contact of the electrode to the instrument blank, thereby eliminating any machining stresses induced by traditional grinding methods. The EDM and ECM processes re-deposit material on the surface as the removed material is being disintegrated and cooled, and results in a recast layer on the flute that has a surface hardness increase of at least about 15%, for example 15–25%, compared to the starting material of the instrument blank, thereby providing a significantly harder and more resilient cutting edge. Moreover, the EDM and ECM processes produce a non-directional surface finish, therefore eliminating inducement of early material failure propagated by directional surface finishes that result from grinding techniques. In addition, the instrument blank is not required to be pre-ground to the desired cross-sectional shape prior to forming the flutes, as must be done in permanently twisting files to achieve desired helical flutes.

Another advantage of EDM and ECM processes, with respect to endodontic instruments, is that by adjusting the different variables associated with EDM and ECM, the surface finish of the instrument blank along with the surface finish of fluted portions of the instrument can be varied from fine to course, resulting in different cutting performances as well as variable surface hardness along the cutting edge of the flutes. Further, by producing different surface patterns or textures on the electrode and the ability of EDM and ECM to transfer the reverse image on the surface of the electrode directly to the instrument blank being processed, different surface textures and patterns may be produced on the surface of the instrument blank being machined by EDM or ECM. Surface texturing and variable surface finishes enhance cutting performance by the instrument. EDM and ECM processes further increase the instrument elasticity. EDM and ECM processes thus offer distinct advantages to the manufacture of endodontic instruments that have not heretofore been recognized.

The material used for the instrument blank may be a wire-like rod comprising a titanium alloy such as superelastic nickel-titanium alloys, or may be a stainless steel or steel alloy. Superelastic materials are advantageously used due to the increased flexibility of such materials.

Figure 4A:
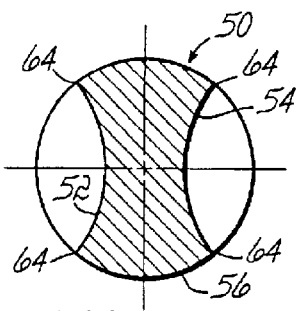
FIGS. 4A–4I are transverse cross-sectional views, perpendicular to the center longitudinal axis of the instrument, formed using the apparatus of FIG. 3.
Figure 4B:
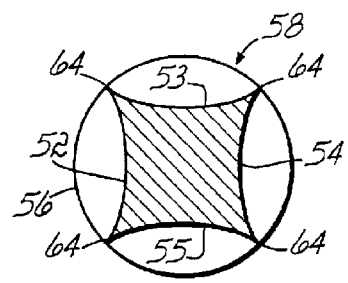
Figure 4C:
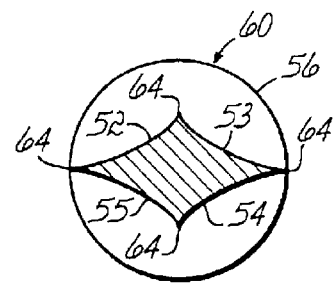
Figure 4D:
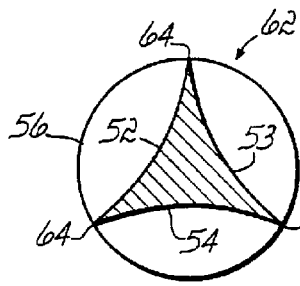

The EDM and ECM processes of the present invention further provide high flexibility with respect to the particular design of the flutes that may be achieved for the instrument. FIGS. 4A–4I provide transverse cross-sectional views of various exemplary flute designs that may be formed in accordance with the invention. FIG. 4A provides a cross section of an instrument 50 having two continuous helical flutes 52, 54 formed in the peripheral surface of instrument blank 56. In the method of the present invention, the first flute 52 is formed by EDM or ECM, and then the instrument blank 56 is indexed 180° and the second flute 54 is formed by EDM or ECM. Two additional flutes 53, 55 may be formed to provide instrument 58 as shown in cross section in FIG. 4B. The method to produce instrument 58 may include forming flute 52 by EDM or ECM, then indexing the blank 56 by 90°; forming the second flute 53, then indexing the blank 56 by 90°; forming the third flute 54, then indexing the blank 56 by 90°; and finally forming the fourth flute 55. Alternatively, the method may include forming the first flute 52, then indexing the blank 56 by 180°; forming the second flute 54, then indexing the blank by 90°; forming the third flute 53, then indexing the blank 56 by 180°; and forming the fourth flute 55. Instrument 60 shown in cross section in FIG. 4C is similar to instrument 58 in that it has four flutes 52, 53, 54, 55, but instead has a rhomboidal transverse cross section. The method for forming instrument 60 includes forming the first flute 52, then indexing the blank 56 by 120°; forming the second flute 53, then indexing the blank 56 by 60°; forming the third flute 54, then indexing the blank 56 by 120°; and finally forming the fourth flute 55. Instrument 62 depicted in cross section in FIG. 4D has three flutes 52, 53, 54 and a triangular transverse cross section. Instrument 62 may be manufactured by indexing the file blank 56 by 120° increments. In each of FIGS. 4A–4D, the machined surfaces or flutes 52, 53, 54, 55 have a concave shape. The apices between the concave surfaces form the helical cutting edges 64, which in each of the figures, include either three or four cutting edges 64. Due to the concave shape of the flutes, the angle of the apices is more acute, which provides a sharp cutting edge 64.

Figure 4E:
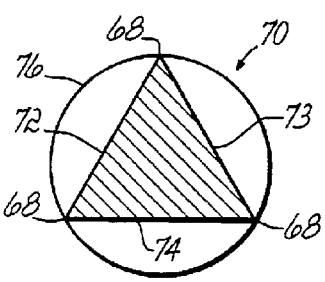
Figure 4F:
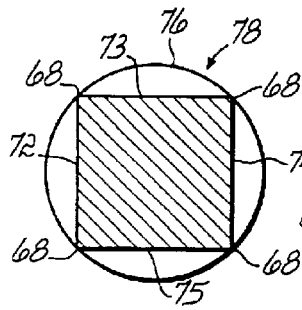
Figure 4G:
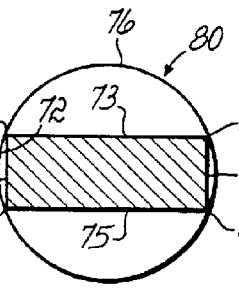
Figure 4H:
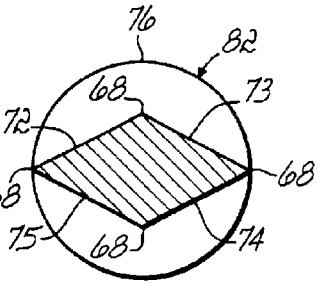

FIGS. 4E–4G depict various transverse cross sections for instruments having flat flutes, as opposed to the concave flutes in FIGS. 4A–4D. The apices between the flat surfaces form the helical cutting edges 68, which in each of the figures, include either three or four cutting edges 68. Due to the flat shape of the flutes, the angle of the apices is less acute, which provides a more rugged cutting edge 68 that will exhibit a longer working life. The acute cutting edges in FIGS. 4A–4D are sharp but weaker due to the lower amount of material, and the less acute cutting edges in FIGS. 4E–4H are less sharp but more rugged with a longer working life.

Instrument 70 depicted in cross section in FIG. 4E has a triangular transverse cross section formed by three flat helical flutes 72, 73, 74, which may be formed by ECM or EDM sequentially with 120° indexing of the instrument blank 76 between forming steps. Instrument 78 depicted in FIG. 4F has a square transverse cross section, for example taken along line 4F of FIG. 2A, and has four flat helical flutes 72, 73, 74, 75. Instrument 78 maybe formed by the same method used to form instrument 58 of FIG. 4B, but using a cutting path that forms flat surfaces rather than concave surfaces. Instrument 80 depicted in FIG. 4G also has four flat helical flutes 72, 73, 74, 75, but has a rectangular transverse cross section. With respect to the method for forming instrument 80, for example, the first flat surface or flute 72 may be formed by EDM or ECM, then the instrument blank 76 is indexed by 90°. The initial depth of cut is increased and the second flat surface or flute 73 is formed by EDM or ECM. Instrument blank 76 is again indexed 90° and the initial depth of cut is reduced to form flute 74. Then, the blank 76 is indexed a final 90° and the initial depth of cut increased to form flute 75. Alternatively, flute 72 may be formed by EDM or ECM, then the instrument blank is indexed by 180° and the flute 74 is formed. The blank 76 is then indexed by 90° and the initial depth of cut increased and flute 73 is formed. Then, the blank 76 is indexed 180° and flute 75 is formed. Instrument 82 depicted in FIG. 4H also has flat helical flutes 72, 73, 74 and 75, but has a rhomboidal transverse cross section. The method for forming instrument 82 includes forming flute 72, then indexing the blank 76 by 120°; forming flute 73, then indexing the blank 76 by 60°; forming flute 74, then indexing the blank 76 by 120°; and finally forming flute 75. It is not necessary to change the initial depth of cut to fabricate the square, triangular and rhomboidal instruments.

Figure 4I:
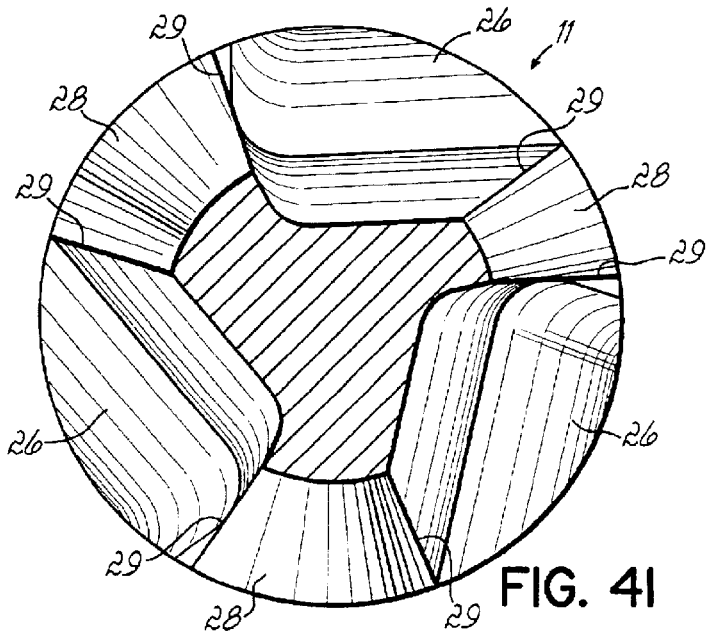

FIG. 4I depicts the transverse cross section along line 41 of the instrument 11 of FIG. 1B having non-helical flutes 26 with concave surfaces. In this exemplary embodiment, the flutes 26 are non-uniformly concave, with convex lands 28 there between. Apices are formed where the flutes 26 meet the lands 28 to form six cutting edges 29. The flutes 26 and thus cutting edges 29 are tapered along the working length 22. The EDM and ECM processes used in accordance with the present invention allow for easy manufacture of endodontic instruments having complicated profiles such as that depicted in FIGS. 1B and 4I. It may be appreciated, however, that other profiles other than that shown may be formed in accordance with the present invention.

In addition to the above embodiments describing the use of EDM and ECM for forming the flutes, the EDM and ECM processes are also useful in forming an instrument blank, regardless of whether twisting or EDM/ECM is subsequently used to form the flutes. Thus, the present invention further provides an endodontic instrument having a plurality of helical flutes prepared by first forming a blank having flute surfaces of the desired transverse cross-section by an EDM or ECM process, and second, twisting the blank to form helical flutes. The flute surfaces are formed by removing at least about 25% of a diameter of a wire or rod at a point of maximum metal removal and redepositing a portion of the removed material to form a recast layer having a hardness of at least about 15% greater than the hardness of the wire or rod material. Twisting may be accomplished, for example, in accordance with U.S. Pat. Nos. 6,149,501 and 5,984,679 or in accordance with the method described above with reference to FIG. 2. The EDM or ECM process used to form the instrument blank results in a recast layer on the blank that has a surface hardness increase of at least about 15%, for example 15–25%, compared to the starting material, thereby providing a significantly harder and more resilient cutting edge after twisting. Moreover, the EDM or ECM process produces a non-directional surface finish, therefore eliminating inducement of early material failure propagated by directional surface finishes that result from grinding techniques.

While the present invention has been illustrated by the description of an embodiment thereof, and while the embodiment has been described in considerable detail, it is not intended to restrict or in any way limit the scope of the appended claims to such detail. Additional advantages and modifications will readily appear to those skilled in the art. The invention in its broader aspects is therefore not limited to the specific details, representative apparatus and method and illustrative examples shown and described. Accordingly, departures may be made from such details without departing from the scope or spirit of Applicant's general inventive concept.

What is claimed is:

1. A method for forming a superelastic endodontic instrument comprising the steps of:

providing an instrument blank formed from a wire of superelastic material, wherein the superelastic material of the instrument blank is in an annealed state comprising a phase structure selected from the group consisting of: a rhombohedral phase, a combination of an austenite phase and a martensite phase, a combination of a rhombohedral phase and an austenite phase, a combination of a rhombohedral phase and a martensite phase, and a combination of a rhombohedral phase, an austenite phase and a martensite phase;

while in the annealed state, twisting the instrument blank to a final twisted configuration for the instrument; and after twisting, heat treating the twisted instrument, followed by rapidly quenching the twisted instrument to a superelastic condition.

2. The method of claim 1 wherein the step of forming the wire is by grinding.

3. The method of claim 1 wherein the superelastic material comprises at least about 40 at.% titanium.

4. The method of claim 3 wherein the superelastic material is a nickel-titanium alloy.

5. The method of claim 4 wherein the nickel-titanium alloy further comprises an element selected from the group consisting of: niobium, copper, iron, chromium, cobalt, vanadium, hafnium and palladium.

6. The method of claim 1 wherein the step of twisting the blank is at a temperature less than about 100 ° C.

7. The method of claim 1 wherein the instrument is provided in an annealed state comprising the rhombohedral phase.

8. A method for forming a superelastic endodontic instrument comprising the steps of:

providing an instrument blank formed from a wire of superelastic material, wherein the superelastic material of the instrument blank is in an annealed state comprising a phase structure selected from the group consisting of: a rhombohedral phase, a combination of an austenite phase and a martensite phase, a combination of a rhombohedral phase and an austenite phase, a combination of a rhombohedral phase and a martensite phase, and a combination of a rhombohedral phase, an austenite phase and a martensite phase;

while in the annealed state, twisting the instrument blank to a final twisted configuration for the instrument; and after twisting, heat treating the twisted instrument, followed by rapidly quenching the twisted instrument to a superelastic condition, wherein the step of forming the wire is by removing material having a first hardness by a method selected from the group consisting of electrical discharge machining, wire electrical discharge machining, electrical discharge grinding and electrochemical machining, including removing at least about 25% of a diameter of the wire at a point of maximum metal removal, and redepositing at least a portion of the removed material on the instrument blank to form a recast layer having a second hardness of at least about 15% greater than the first hardness.

9. A method for forming a superelastic endodontic instrument comprising the steps of:

providing an instrument blank formed from a wire of superelastic material, wherein the superelastic material of the instrument blank is in an annealed state comprising a phase structure selected from the group consisting of: a rhombohedral phase, a combination of an austenite phase and a martensite phase, a combination of a rhombohedral phase and an austenite phase, a combination of a rhombohedral phase and a martensite phase, and a combination of a rhombohedral phase, an austenite phase and a martensite phase:

while in the annealed state, twisting the instrument blank to a final twisted configuration for the instrument; and after twisting, heat treating the twisted instrument, followed by rapidly quenching the twisted instrument to a superelastic condition.

wherein the step of twisting the blank is at ambient temperature.

10. A method for forming a superelastic endodontic instrument comprising the steps of:

providing an instrument blank formed from a wire of superelastic material, wherein the superelastic material of the instrument blank is in an annealed state comprising a phase structure selected from the group consisting of: a rhombohedral phase, a combination of an austenite phase and a martensite phase, a combination of a rhombohedral phase and an austenite phase, a combination of a rhombohedral phase and a martensite phase, and a combination of a rhombohedral phase, an austenite phase and a martensite phase;

while in the annealed state, twisting the instrument blank to a final twisted configuration for the instrument: and after twisting, heat treating the twisted instrument, followed by rapidly quenching the twisted instrument to a superelastic condition, wherein the step of heat treating the twisted instrument is at a temperature in the range of about 400–600° C.

11. A method for forming a superelastic endodontic instrument comprising the steps of:

providing an instrument blank formed from a wire of superelastic material, wherein the superelastic material of the instrument blank is in an annealed state comprising a phase structure selected from the group consisting of: a rhombohedral phase, a combination of an austenite phase and a martensite phase, a combination of a rhombohedral phase and an austenite phase, a combination of a rhombohedral phase and a martensite phase, and a combination of a rhombohedral phase, an austenite phase and a martensite phase;

while in the annealed state, twisting the instrument blank to a final twisted configuration for the instrument;

after twisting, heat treating the twisted instrument, followed by rapidly quenching the twisted instrument to a superelastic condition; and after rapidly quenching, heating the twisted instrument to a temperature in the range of about 150–300° C. to relieve stress therein.

12. A method for forming a superelastic endodontic instrument comprising the steps of:

annealing a superelastic material at a temperature in the range of about 250–700° C. to an annealed state comprising a phase structure selected from the group consisting of: a rhombohedral phase, a combination of an austenite phase and a martensite phase, a combination of a rhombohedral phase and an austenite phase, a combination of a rhombohedral phase and a martensite phase, and a combination of a rhombohedral phase, an austenite phase and a martensite phase, and cooling the annealed material to ambient temperature;

forming the superelastic material into an instrument blank;

while in the annealed state, twisting the blank at a temperature less than about 100° C. to a final twisted configuration for the instrument;

after twisting, heat treating the twisted instrument at a temperature in the range of about 300–800° C., followed by rapidly quenching the twisted instrument to a superelastic condition.

13. The method of claim 12 wherein the step of annealing the superelastic material is at a temperature in the range of about 350–550° C.

14. The method of claim 12 wherein the step of annealing the superelastic material is at a temperature sufficient to provide a phase structure including the rhombohedral phase.

15. The method of claim 12 wherein the step of forming the superelastic material is performed before the step of annealing the superelastic material.

16. The method of claim 15 wherein the step of forming the superelastic material is by removing material having a first hardness by a method selected from the group consisting of electrical discharge machining, wire electrical discharge machining, electrical discharge grinding and electrochemical machining, including removing at least about 25% of a diameter of a starting material at a point of maximum metal removal, and redepositing at least a portion of the removed material on the instrument blank to form a recast layer having a second hardness of at least about 15% greater than the first hardness.

17. The method of claim 15 wherein the step of forming the superelastic material is by grinding.

18. The method of claim 12 wherein the step of forming the superelastic material is performed after the step of annealing the superelastic material.

19. The method of claim 18 wherein the step of forming the superelastic material is by removing material having a first hardness by a method selected from the group consisting of electrical discharge machining, wire electrical discharge machining, electrical discharge grinding and electrochemical machining, including removing at least about 25% of a diameter of a starting material at a point of maximum metal removal, and redepositing at least a portion of the removed material on the instrument blank to form a recast layer having a second hardness of at least about 15% greater than the first hardness.

20. The method of claim 18 wherein the step of forming the superelastic material is by grinding.

21. The method of claim 12 wherein the step of twisting the blank is at ambient temperature.

22. The method of claim 12 wherein the step of heat treating the twisted instrument is at a temperature in the range of about 400–600° C.

23. The method of claim 12 further comprising, after rapidly quenching, heating the twisted instrument to a temperature in the range of about 150–300° C. to relieve stress therein.

24. The method of claim 23 wherein the twisted instrument is heated for a period of about 2–6 hours.

25. The method of claim 12 wherein the superelastic material comprises at least about 40 at. % titanium.

26. The method of claim 25 wherein the superelastic material is a nickel-titanium alloy.

27. The method of claim 26 wherein the nickel-titanium alloy further comprises an element selected from the group consisting of: niobium, copper, iron, chromium, cobalt, vanadium, hafnium and palladium.

28. A method for forming a superelastic endodontic instrument comprising the steps of:

annealing a nickel-titanium alloy at a temperature in the range of about 250–700° C. to an annealed state comprising a phase structure selected from the group consisting of: a rhombohedral phase, a combination of an austenite phase and a martensite phase, a combination of a rhombohedral phase and an austenite phase, a combination of a rhombohedral phase and a martensite phase, and a combination of a rhombohedral phase, an austenite phase and a martensite phase, and cooling the annealed alloy to ambient temperature;

forming the annealed alloy into an instrument blank;

twisting the instrument blank at ambient temperature to a final twisted configuration for the instrument;

heat treating the twisted instrument at a temperature in the range of about 300–800° C., followed by rapidly quenching the twisted instrument to a superelastic condition.

29. The method of claim 28 wherein the step of annealing the nickel-titanium alloy is at a temperature in the range of about 350–550° C.

30. The method of claim 28 wherein the step of annealing the nickel-titanium alloy is at a temperature sufficient to provide a phase structure including the rhombohedral phase.

31. The method of claim 28 wherein the step of forming the alloy is by removing material having a first hardness by a method selected from the group consisting of electrical discharge machining, wire electrical discharge machining, electrical discharge grinding and electrochemical machining, including removing at least about 25% of a diameter of a starting material at a point of maximum metal removal, and redepositing at least a portion of the removed material on the instrument blank to form a recast layer having a second hardness of at least about 15% greater than the first hardness.

32. The method of claim 28 wherein the step of forming the alloy is by grinding.

33. The method of claim 28 wherein the step of heat treating the twisted instrument is at a temperature in the range of about 400–600° C.

34. The method of claim 28 further comprising, after rapidly quenching, heating the twisted instrument to a temperature in the range of about 150–300° C. to relieve stress therein.

35. The method of claim 34 wherein the twisted instrument is heated for a period of about 2–6 hours.

36. The method of claim 28 wherein the nickel-titanium alloy comprises at least about 40 at. % titanium.

37. The method of claim 36 wherein the nickel-titanium alloy further comprises an element selected from the group consisting of: niobium, copper, iron, chromium, cobalt, vanadium, hafnium and palladium.

38. A method for forming a superelastic endodontic instrument comprising the steps of:

forming an instrument blank from a nickel-titanium alloy wire;

annealing the instrument blank at a temperature in the range of about 250–700° C. to an annealed state comprising a phase structure selected from the group consisting of: a rhombohedral phase, a combination of an austenite phase and a martensite phase, a combination of a rhombohedral phase and an austenite phase, a combination of a rhombohedral phase and a martensite phase, and a combination of a rhombohedral phase, an austenite phase and a martensite phase, and cooling the annealed instrument blank to ambient temperature;

twisting the annealed instrument blank at ambient temperature to a final twisted configuration for the instrument;

heat treating the twisted instrument at a temperature in the range of about 300–800° C., followed by rapidly quenching the twisted instrument to a superelastic condition.

39. The method of claim 38 wherein the step of annealing the instrument blank is at a temperature in the range of about 350–550° C.

40. The method of claim 38 wherein the step of annealing the instrument blank is at a temperature sufficient to provide a phase structure including the rhombohedral phase.

41. The method of claim 38 wherein the step of forming the alloy wire is by removing material having a first hardness by a method selected from the group consisting of electrical discharge machining, wire electrical discharge machining, electrical discharge grinding and electrochemical machining, including removing at least about 25% of a diameter of the alloy wire at a point of maximum metal removal, and redepositing at least a portion of the removed material on the instrument blank to form a recast layer having a second hardness of at least about 15% greater than the first hardness.

42. The method of claim 38 wherein the step of forming the alloy wire is by grinding.

43. The method of claim 38 wherein the step of heat treating the twisted instrument is at a temperature in the range of about 400–600° C.

44. The method of claim 38 further comprising, after rapidly quenching, heating the twisted instrument to a temperature in the range of about 150–300° C. to relieve stress therein.

45. The method of claim 44 wherein the twisted instrument is heated for a period of about 2–6 hours.

46. The method of claim 38 wherein the nickel-titanium alloy comprises at least about 40 at. % titanium.

47. The method of claim 46 wherein the nickel-titanium alloy further comprises an element selected from the group consisting of: niobium, copper, iron, chromium, cobalt, vanadium, hafnium and palladium.

* * * * *